(12) United States Patent
Schrodi

(10) Patent No.: US 9,273,081 B2
(45) Date of Patent: Mar. 1, 2016

(54) METHOD FOR IN-SITU FORMATION OF METATHESIS CATALYSTS

(71) Applicant: Yann Schrodi, Northridge, CA (US)

(72) Inventor: Yann Schrodi, Northridge, CA (US)

(*) Notice: Subject to any disclaimer, the term of this patent is extended or adjusted under 35 U.S.C. 154(b) by 0 days.

(21) Appl. No.: 14/606,580

(22) Filed: Jan. 27, 2015

(65) Prior Publication Data
US 2015/0299235 A1 Oct. 22, 2015

Related U.S. Application Data

(63) Continuation of application No. 13/636,918, filed as application No. PCT/US2011/029690 on Mar. 24, 2011.

(60) Provisional application No. 61/340,951, filed on Mar. 24, 2010.

(51) Int. Cl.
*C07F 15/00* (2006.01)
*B01J 31/22* (2006.01)

(52) U.S. Cl.
CPC ......... *C07F 15/0046* (2013.01); *B01J 31/2265* (2013.01); *B01J 2231/543* (2013.01); *B01J 2531/821* (2013.01)

(58) Field of Classification Search
CPC ............................. C07F 15/0046; B01J 31/2265
USPC ................................................... 556/22, 136
See application file for complete search history.

(56) References Cited

U.S. PATENT DOCUMENTS 8,237,003 B2  8/2012  Holtcamp et al.

FOREIGN PATENT DOCUMENTS

WO  2009/124853 A1  10/2009

OTHER PUBLICATIONS

Bachmann et al., "The Pinacol-Pinacolone Rearrangement. VI. The Rearrangement of Symmetrical Aromatic Pinacols," J. Am. Chem. Soc. 56:2081-2084 (1934).
Boeda et al., "Ruthenium-indenylidene complexes: powerful tools for metathesis transformations," Feature Article, Chem. Commun., The Royal Society of Chemistry, pp. 2726-2740 (May 20, 2008).
Chatterjee et al., "Synthesis of Functionalized Olefins by Cross and Ring-Closing Metatheses," J. Am. Chem. Soc. 122:3783-3784 (2000).
Demonceau et al., "Novel Ruthenium-Based Catalyst Systems for the Ring-Opening Metathesis Polymerization of Low-Strain Cyclic Olefins," Macromolecules 30:3127-3136 (1997).
Dragutan et al., "Ruthenium Allenylidene Complexes," Platinum Met. Rev. 50:81-94 (2006).
Fürstner et al., "Ruthenium Carbene Complexes with N,N'-Bis(mesityl)imidazol-2-ylidene Ligands: RCM Catalysts of Extended Scope," J. Org. Chem. 65:2204-2207 (2000).
Fürstner et al., "Cationic Ruthenium Allenylidene Complexes as Catalysts for Ring Closing Olefin Meathesis," Chem. Eur. J. 6:1847-1857 (2000).
Fürstner et al., "Indenylidene Complexes of Ruthenium: Optimized Synthesis, Structure Elucidation, and Performance as Catalysts for Olefin Metathesis—Application to the Synthesis of the ADE-Ring System of Nakadomarin A," Chem. Eur. J. 7:4811-4820 (2001).
Furstner et al., "Bidentate Ruthenium Vinylcarbene Catalysts Derived from Enyne Metathesis", Organometallics 24 (16):4065-4071 (2005).
Garber et al., "Efficient and Recyclable Monomeric and Dendritic Ru-Based Metathesis Catalysts," J. Am. Chem. Soc. 122:8168-8179 (2000).
Grubbs, "Olefin-Metathesis Catalysts for the Preparation of Molecules and Materials (Nobel Lecture 2005)," Adv. Synth. Catal. 349:34-40 (2007).
Jimenez et al., "A Most Convenient and Atom-Economic Preparation of a Highly Active Ring-Closing Metathesis Catalyst", Organometallics, 29(16):3471-3473 (2010).
Kabro et al., "Ruthenium-Indenylidene Olefin Metathesis Catalyst with Enhanced Thermal Stability", Full Paper, Chem. Eur. J. 16:12255-12261 (2010).

(Continued)

*Primary Examiner* — Porfirio Nazario Gonzalez
(74) *Attorney, Agent, or Firm* — J.A. Lindeman & Co., PLLC

(57) ABSTRACT

Synthetic methods for the in-situ formation of olefin metathesis catalysts are disclosed, as well as the use of such catalysts in metathesis reactions of olefins and olefin compounds. In one aspect, a method is provided for synthesizing an organometallic compound of the formula

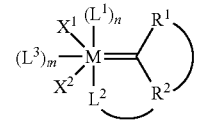

comprising contacting a precursor compound of the formula $(X^1X^2ML_jL^1{}_kL^3{}_m)_i$ with an acetylenic compound comprising a chelating moiety, optionally, in the presence of a neutral electron donor, wherein M is a Group 8 transition metal, L, $L^1$, $L^2$, and $L^3$ are neutral electron donors, $X^1$ and $X^2$ are anionic ligands, j is 1, 2, or 3; k is zero, 1, or 2; m is zero or 1; n is 1 or 2; and i is an integer; with the proviso that k is zero when the precursor compound is contacted with the acetylenic compound in the presence of the neutral electron donor, and $R^1$ and $R^2$ are independently selected from hydrocarbyl, substituted hydrocarbyl, heteroatom-containing hydrocarbyl, substituted heteroatom-containing hydrocarbyl, and functional groups, wherein $R^1$ and $R^2$ are linked and together form one or more cyclic groups, $R^2$ and $L^2$ are linked and together form one or more cyclic groups, and any other two or more of $X^1$, $X^2$, $L^1$, $L^2$, $L^3$, $R^1$, and $R^2$ can be taken together to form one or more cyclic groups. The invention has utility in the fields of catalysis, organic synthesis, polymer chemistry, and industrial and fine chemicals chemistry.

8 Claims, 1 Drawing Sheet

(56) References Cited

OTHER PUBLICATIONS

Katayama et al., "Convenient Routes to Vinylideneruthenium Dichlorides with Basic and Bulky Tertiary Phosphine Ligands (PPri3 and PCy3)," Organometallics 17:5190-5196 (1998).

Katayama et al., "Vinylideneruthenium complexes in catalysis," Coord. Chem. Rev. 248:1703-1715 (2004).

Kingsbury et al., "A Recyclable Ru-Based Metathesis Catalyst", J. Am. Chem. Soc. 121(4):791-799 (1999).

Kirkland et al., "Effects of Olefin Substitution on the Ring-Closing Metathesis of Dienes," J. Org. Chem. 62:7310-7318 (1997).

Krishnamurthy et al., "Synthesis and Testing of Novel Phenyl Substituted Side-Chain Analogues of Classical Cannabinoids," Bioorg. Med. Chem. Lett. 13:3487-3490 (2003).

Lipshutz et al., "PQS: A New Platform for Micellar Catalysis. RCM Reactions in Water, with Catalyst Recycling," Org. Lett. 11(3):705-708 (2009).

Li et al., "Organolanthanide-Catalyzed Intra- and Intermolecular Tandem C—N and C—C Bond-Forming Processes of Aminodialkenes, Aminodialkynes, Aminoalkeneynes, and Aminoalkynes. New Regiospecific Approaches to Pyrrolizidine, Indolizidine, Pyrrole, and Pyrazine Skeletons," J. Am. Chem. Soc. 120:1757-1771 (1998).

Louie et al., "Highly Active Metathesis Catalysts Generated In Situ from Inexpensive and Air-Stable Precursors," Angew. Chem. Int. Ed. 40:247-249 (2001).

Monsaert et al., "Indenylidene-Ruthenium Complexes Bearing Saturated N-Heterocyclic Carbenes: Synthesis and Catalytic Investigation in Olefin Metathesis Reactions," Eur. J. Inorg. Chem. 432-440 (2008).

Paquette et al., "Direct Comparison of the Response of Bicyclic Sultam and Lactam Dienes to Photoexcitation. Concerning the Propensity of Differing Bond Types to Bridgehead Nitrogen for Homolytic Cleavage," J. Org. Chem. 71:8438-8445 (2006).

Ritter et al., "A Standard System of Characterization for Olefin Metathesis Catalysts," Organometallics 25:5740-5745 (2006).

Schanz et al., "Coordinatively Unsaturated 16-Electron Ruthenium Allenylidene Complexes: Synthetic, Structural, and Catalytic Studies," Organometallics 18:5187-5190 (1999).

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," Org.Lett. 1:953-956 (1999).

Schrodi et al., "Evolution and Applications of Second-Generation Ruthenium Olefin Metathesis Catalysts," Aldrichim. Acta 40:45-52 (2007).

Schwab et al., "Synthesis and Applications of RuCl2(=CHR')(PR3)2: The Influence of the Alkylidene Moiety on Metathesis Activity," J. Am. Chem. Soc. 118:100-110 (1996).

Treilhou et al., "Use of Biological Catalysts for the Preparation of Chiral Molecules. 8. Preparation of Propargylic Alcohols. Application in the Total Synthesis of Leukotriene B4," J. Org. Chem. 57:3203-3208 (1992).

Wang et al., "A New One Pot Method for the Conversion of Aldehydes into Nitriles Using Hydroxyamine and Phthalic Anhydride," Tetrahedron Lett. 39:4047-4050 (1998).

PCT International Search Report for PCT/US2011/029690, dated Nov. 21, 2011.

PCT International Preliminary Report on Patentability, and Written Opinion for PCT/US2011/029690, dated Sep. 25, 2012.

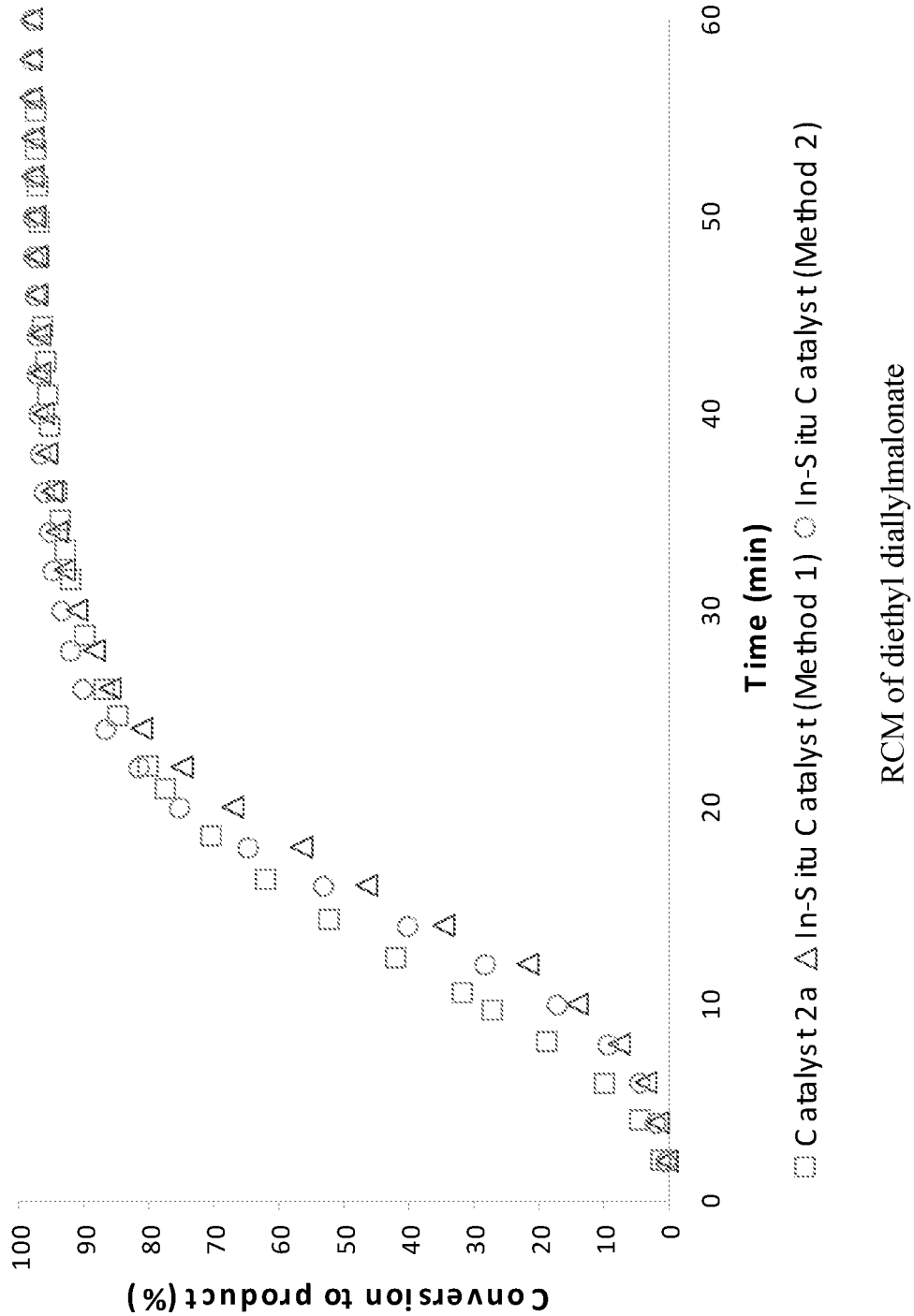

METHOD FOR IN-SITU FORMATION OF METATHESIS CATALYSTS

TECHNICAL FIELD

This invention relates generally to organometallic olefin metathesis catalysts, and more particularly to the in-situ formation of such olefin metathesis catalysts, as well as the use of such catalysts in metathesis reactions of olefins and olefin compounds. The invention has utility in the fields of catalysis, organic synthesis, polymer chemistry, and industrial and fine chemicals chemistry.

BACKGROUND

Olefin metathesis has become an exceptionally powerful and applicable method for the formation of carbon-carbon bonds in organic and polymer synthesis. Ruthenium-based complexes (1-3) are the most commonly employed olefin metathesis catalysts in academic and industrial laboratories, because they can be handled in air and are tolerant of various organic functional groups.

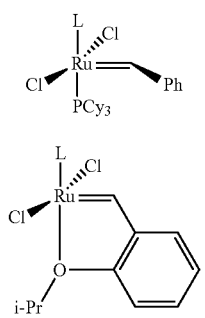

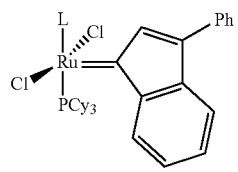

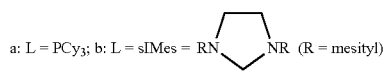

a: L = PCy₃; b: L = sIMes = RN⌒NR (R = mesityl)

(see (a) Schrodi, Y.; Pederson, R. L. *Aldrichim. Acta* 2007, 40, 45-52. (b) Grubbs, R. H. *Adv. Synth. Catal.* 2007, 349, 34-40). However, the syntheses of these complexes are relatively cumbersome, usually involving more than one step and requiring isolation of the catalysts to remove catalyst-inhibiting by-products such as liberated phosphine ligands (Scheme 1). (see, e.g., (a) Schwab, P.; Grubbs, R. H.; Ziller, J. W. *J. Am. Chem. Soc.* 1996, 118, 100-110. (b) Scholl, M.; Ding, S.; Lee, C. W.; Grubbs, R. H. *Org. Lett.* 1999, 1, 953-956. (c) Chatterjee, A. K.; Morgan, J. P.; Scholl, M.; Grubbs, R. H., *J. Am. Chem. Soc.* 2000, 122, 3783-3784. (d) Kingsbury, J. S.; Harrity, J. P. A.; Bonitatebus, P. J., Jr.; Hoveyda, A. H., *J. Am. Chem. Soc.* 1999, 121 (4), 791-799. (e) Garber, S. B.; Kingsbury, J. S.; Gray, B. L.; Hoveyda, A. H. *J. Am. Chem. Soc.* 2000, 122, 8168-8179. (f) Fürstner, A.; Guth, O.; Duffels, A.; Seidel, G.; Liebl, M.; Gabor, B.; Mynott, R., *Chem.-Eur. J.* 2001, 7, 4811-4820. (g) Fürstner, A.; Thiel, O. R.; Ackermann, L.; Schanz, H.-J.; Nolan, S. P., *J. Org. Chem.* 2000, 65, 2204-2207. (h) Monsaert, S.; Drozdzak, R.; Dragutan, V.; Dragutan, I.; Verpoort, F., *Eur. J. Inorg. Chem.* 2008, 432-440).

Scheme 1. Preparation of ruthenium-based catalysts 1-3

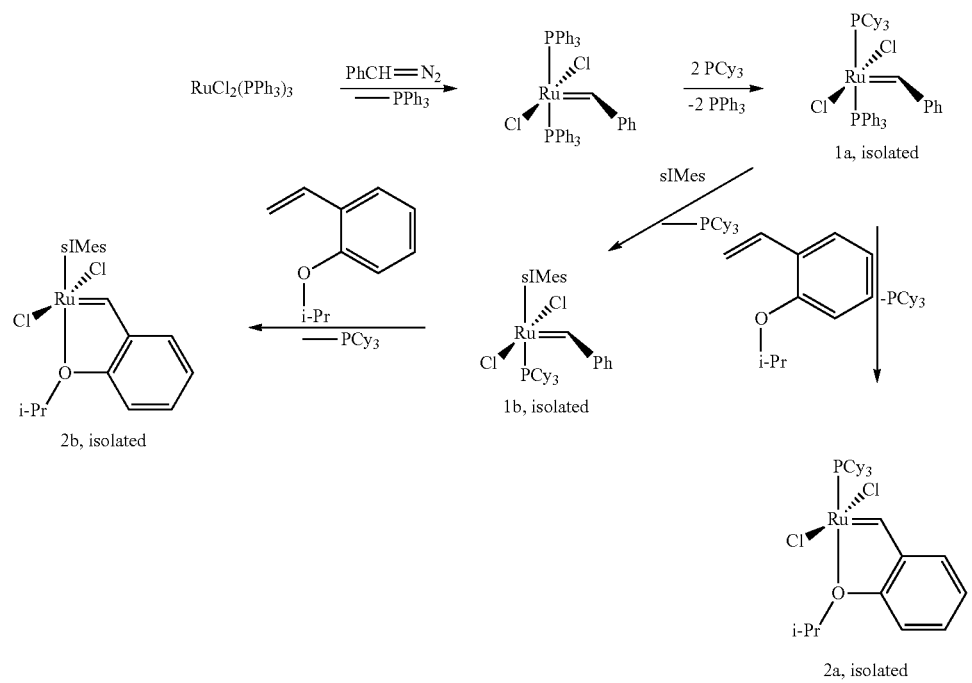

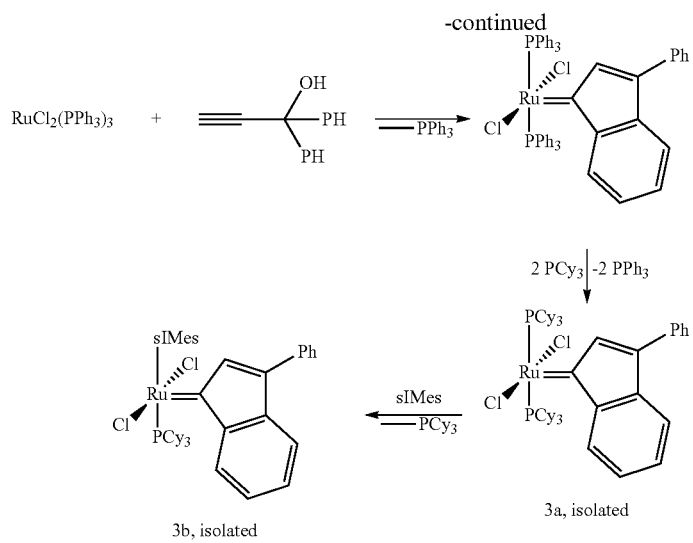

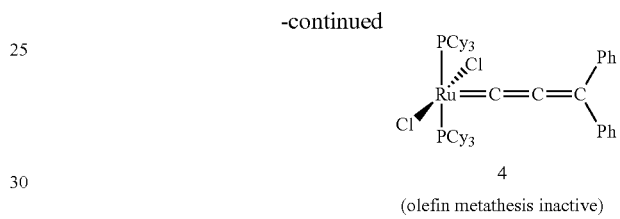

4
(olefin metathesis inactive)

Therefore, a one-step procedure that forms highly active olefin metathesis catalysts and does not require purification or isolation would provide certain advantages. Ideally, the new procedure should be as atom-economic as possible. In particular, a new method that requires only one equivalent of expensive ligands (e.g., $PCy_3$) per ruthenium center would be desirable.

Previous attempts to generate olefin metathesis catalysts in situ focused on the preparation of ruthenium vinylidene (see (a) Katayama, H.; Ozawa, F., *Coord. Chem. Rev.* 2004, 248, 1703-1715. (b) Katayama, H.; Ozawa, F., *Organometallics* 1998, 17, 5190-5196. (c) Louie, J.; Grubbs, R. H., *Angew. Chem., Int. Ed.* 2001, 40, 247-249.) and allenylidene species (see (a) Dragutan, I.; Dragutan, V., Platinum Met. Rev. 2006, 50, 81-94. (b) Fürstner, A.; Liebl, M.; Lehmann, C. W.; Picquet, M.; Kunz, R.; Bruneau, C.; Touchard, D.; Dixneuf, P. H., *Chem.-Eur. J.* 2000, 6, 1847-1857. (c) Schanz, H.-J.; Jafarpour, L.; Stevens, E. D.; Nolan, S. P., *Organometallics* 1999, 18, 5187-5190). However, these types of complexes proved less active in olefin metathesis than their ruthenium-alkylidene counterparts. For example, ruthenium allenylidene complex 4 can be very conveniently prepared in a one-step procedure involving the treatment of [RuCl2(p-cymene)]2 with 1,1-diphenylprop-2-yn-1-ol in the presence of two equivalents of $PCy_3$ (Scheme 2). (See Schanz, H.-J.; Jafarpour, L.; Stevens, E. D.; Nolan, S. P., Organometallics 1999, 18, 5187-5190). Unfortunately, 4 is inactive in olefin metathesis although its chemical isomer-ruthenium-indenylidene complex 3a-shows good activity. (See; and Schanz, H.-J.; Jafarpour, L.; Stevens, E. D.; Nolan, S. P., Organometallics 1999, 18, 5187-5190).

Scheme 2. One-step synthesis of ruthenium allenylidene 4

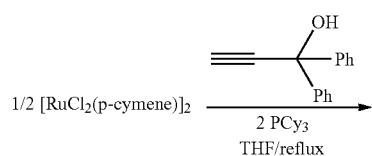

Recently the Schrodi and Bruneau groups have published interesting chelating indenylidene catalysts. (See Jimenez, L. R.; Gallon, B. J.; Schrodi, Y. *Organometallics* 2010, 29, 3471-3473, incorporated herein by reference, and Kabro, A.; Roisnel, T.; Fischmeister, C.; Bruneau, C. *Chem.-Eur. J.* 2010, 16, 12255-12261).

Despite the advances achieved in the preparation of olefin metathesis catalysts, a continuing need exists for new synthetic methods for preparing such catalysts. Of particular interest are methods that provide techniques for the preparation of new catalysts, while also providing for better utilization of reactants and improved product yields.

SUMMARY OF THE DISCLOSURE

Accordingly, the invention is directed to addressing one or more of the aforementioned concerns, and, in one embodiment, provides a method for preparing an organometallic compound, such as an olefin metathesis catalyst, by contacting a precursor compound with an acetylenic compound comprising a chelating moiety, optionally in the presence of a neutral electron donor.

In general, the method involves the synthesis of an organometallic compound of the formula

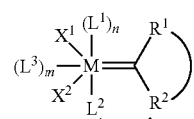

prepared by contacting a precursor compound of the formula $(X^1X^2ML^1_jL^1_kL^3_m)_i$ with an acetylenic compound comprising a chelating moiety, optionally, in the presence of a neutral electron donor $L^1$; wherein, M is a Group 8 transition metal;

L, $L^1$, $L^2$, and $L^3$ are neutral electron donors;

j is 1, 2, or 3; k is zero, 1, or 2; m is zero or 1; n is 1 or 2; and i is an integer; with the proviso that k is zero when the precursor compound is contacted with the acetylenic compound in the presence of the neutral electron donor $L^1$;

$X^1$ and $X^2$ are anionic ligands; and $R^1$ and $R^2$ are independently selected from hydrocarbyl, substituted hydrocarbyl, heteroatom-containing hydrocarbyl, substituted heteroatom-containing hydrocarbyl, and functional groups, wherein $R^1$ and $R^2$ are linked and together form one or more cyclic groups, $R^2$ and $L^2$ are linked and together form one or more cyclic groups, and any other two or more of $X^1$, $X^2$, $L^1$, $L^2$, $L^3$, $R^1$, and $R^2$ can be taken together to form one or more cyclic groups.

In another aspect, the invention provides novel organometallic compounds according to the above structure.

In a further aspect, the invention provides a method for performing a catalytic metathesis reaction comprising contacting at least one olefin or olefinic compound with the metathesis catalyst of the invention.

BRIEF DESCRIPTION OF THE DRAWINGS

FIG. 1 depicts RCM results for diethyl diallylmalonate as described in the examples.

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, Or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S— alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_5$-$C_{24}$ arylsulfonyl (—$SO_2$-aryl), boryl (—$BH_2$), borono (—$B(OH)_2$), boronato (—$B(OR)_2$ where R is alkyl or other hydrocarbyl), phosphono (—$P(O)(OH)_2$), phosphonato (—$P(O)(O^-)_2$), phosphinato (—$P(O)(O^-)$), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

A "reaction system," as used herein, refers to a functionally related group of components.

Methods and Compositions

The olefin metathesis catalyst complex that may be prepared according to the invention is a Group 8 transition metal complex generally having the structure of formula (I)

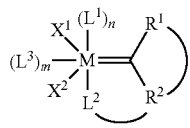

(I)

in which the various substituents are as follows:
M is a Group 8 transition metal;
$L^1$, $L^2$, and $L^3$ are neutral electron donor ligands;
m is zero or 1;
n is 1 or 2;
$X^1$ and $X^2$ are anionic ligands; and $R^1$ and $R^2$ are independently selected from hydrocarbyl, substituted hydrocarbyl, heteroatom-containing hydrocarbyl, substituted heteroatom-containing hydrocarbyl, and functional groups, wherein $R^1$ and $R^2$ are taken together to form one or more cyclic groups, $R^2$ and $L^2$ are taken together to form one or more cyclic groups, and any other two or more of $X^1$, $X^2$, $L^1$, $L^2$, $R^1$, and $R^2$ can be taken together to form one or more cyclic groups.

In certain embodiments, the catalysts contain Ru or Os as the Group 8 transition metal. Ru is particularly preferred for some embodiments.

A first group of catalysts have the structure of formula (I), in which M and n are as described above, and $X^1$, $X^2$, $L^1$, $L^2$, $L^3$, $R^1$, and $R^2$ are described as follows.

For the first group of catalysts, n is 1, and $L^1$, $L^2$, and $L^3$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, thioether, and thiocarbonyl. Exemplary ligands are trisubstituted phosphines.

Suitable phosphines include, but are not limited to, phosphines of the formula $PR^a R^b R^c$, wherein $R^a$, $R^b$, and $R^c$ are each independently selected from aryl, substituted aryl, alkyl, substituted alkyl, cycloalkyl, substituted cycloalkyl, heterocycles, and substituted heterocycles $X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

Any two or more (typically two, three, or four) of $X^1$, $X^2$, $L^1$, $L^2$, $L^3$, $R^1$, and $R^2$ can be taken together to form a cyclic group, including bidentate or multidentate ligands, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts according to the general structure of formula (I), wherein $L^1$ is a carbene ligand having the structure of formula (II)

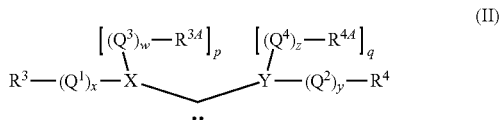

(II)

such that the complex may have the structure of formula (III)

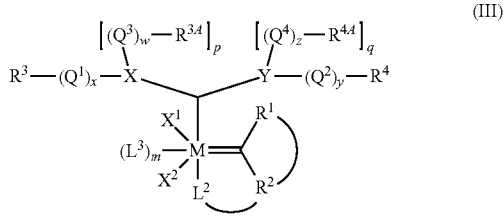

(III)

wherein M, m, $X^1$, $X^2$, $L^2$, $L^3$, $R^1$, and $R^2$ are as defined for the first group of catalysts, and the remaining substituents are as follows. X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In certain embodiments, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group.

Preferably, $R^{3A}$ and $R^{4A}$ are linked to form a cyclic group so that the carbene ligand has the structure of formula (IV)

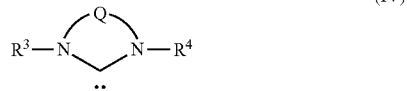

(IV)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands and acyclic diaminocarbene ligands suitable as $L^1$ thus include, but are not limited to, the following where DIPP is diisopropylphenyl and Mes has been defined earlier:

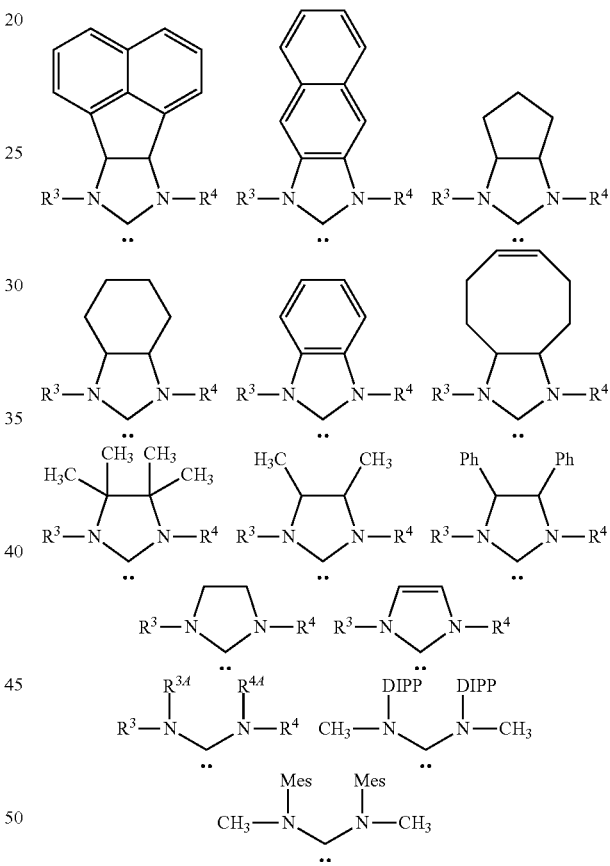

Examples of N-heterocyclic carbene ligands and acyclic diaminocarbene ligands suitable as $L^1$ thus include, but are not limited to, the following where DIPP is diisopropylphenyl and Mes has been defined earlier:

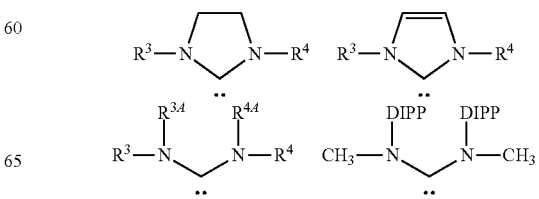

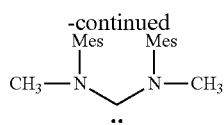

In certain embodiments, preferred complexes have the structure of formula (V)

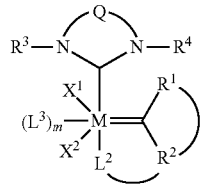

(V)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl, diisopropylphenyl, mono-ortho tolyl and mono-ortho isopropylphenyl.

Complexes wherein T is coordinated to the metal include metathesis-active metal carbene complexes that may be described by the formula

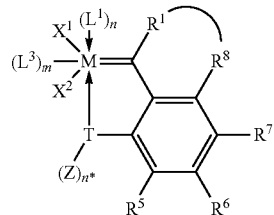

(VI)

wherein,

M is a Group 8 transition metal, particularly Ru or Os, or, more particularly, Ru;

$X^1$, $X^2$, $R^1$, and $L^1$ are as previously defined herein;

T is a heteroatom selected from N, O, S, and P; preferably T is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, and any combination of $R^1$, $R^2$, $R^5$, $R^6$, $R^7$, and $R^8$ can be linked to form one or more cyclic groups;

n* is 1 or 2, such that n is 1 for the divalent heteroatoms O or S, and n is 2 for the trivalent heteroatoms N or P;

Z is selected from hydrogen, alkyl, aryl, functionalized alkyl, and functionalized aryl, wherein the functional group(s) are independently selected from alkyl, aryl, alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; and wherein any combination or combinations of M, $X^1$, $X^2$, $L^1$, T, Z, $R^1$, $R^2$, $R^5$, $R^6$, and $R^7$ are linked.

Complexes wherein T and $L^3$, $L^1$ and $L^3$, and $X^1$ and $L^3$ are coordinated to the metal are examples of the fourth group of catalysts. These metathesis-active metal carbene complexes include the formula VII structures,

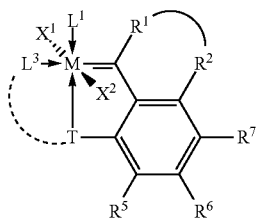 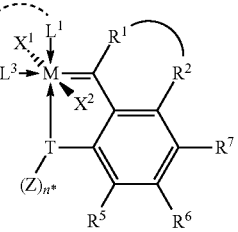

(VII)

-continued

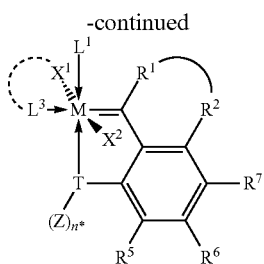

wherein,

M is a Group 8 transition metal, particularly Ru or Os, or, more particularly, Ru;

$X^1, X^2, T, L^1, Z, n^*, R^1, R^2, R^5, R^6,$ and $R^7$ are as previously defined herein;

$L^3$ is a neutral coordinating ligand that is optionally linked to $X^1$, $X^2$, T, $L^1$, $R^1$, $R^2$, $R^5$, $R^6$, and $R^7$; and wherein any combination of M, T, $X^1$, $X^2$, $L^1$, $L^3$, $R^1$, $R^2$, $R^5$, $R^6$, and $R^7$ can form cyclic intermediates.

In general, organic acetylenic compounds useful in the invention may contain a chelating moiety of the formula (VII)

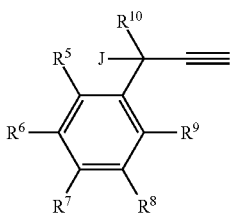

(VII)

wherein,

J is a leaving group;

$R^5$ to $R^9$ are as defined above, and may contain $-T-(Z)_n^*$; and $R^{10}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{10}$ is aryl or heteroaryl, $R^{10}$ may be substituted with any combination of $R^5$, $R^6$, $R^7$, $R^8$ and $R^9$ and can be linked with any of $R^5$, $R^6$, $R^7$, $R^8$, and $R^9$ to form one or more cyclic groups.

Examples of suitable leaving groups include, but are not limited to, hydroxyl, halide, ester, perhalogenated phenyl, acetate, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, J is selected from hydroxyl, halide, $CF_3CO_2$, $CH_3CO_2$, $CFH_2CO_2$, $(CH_3)_3CO$, $(CF_3)_2(CH_3)CO$, $CF_3)(CH_3)_2CO$, PhO, MeO, EtO, tosylate, mesylate, or trifluoromethane-sulfonate. In particular embodiments, J is advantageously hydroxyl (OH).

Preferred organic acetylenic compounds are of the formula,

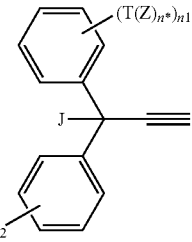

wherein,

T, Z, and n* are as defined above;

n1 is an integer from 1 to 5;

n2 is an integer from 0 to 5; and

R* is selected from $R^5$, $R^6$, $R^7$, $R^8$, and $R^9$, or combinations thereof, as defined above.

Preferred R* and $T-(Z)_n^*$ groups generally include hydrogen and alkoxy groups, more specifically, H and $C_1$-$C_{10}$ alkoxy groups that may be linear and/or include cycloclkyl groups, including methoxide (MeO), ethoxide (EtO), n-propoxide (PropO), isopropoxide (i-PropO), n-butoxide (n-BuO), isobutoxide (i-BuO), t-butoxide (t-BuO), hexyl oxide (HexO), octyl oxide (OctO), decyl oxide (DecylO), cyclopentyl oxide (CpO), and cyclohexyl oxide (CyO). Each of the $R^5$ to $R^9$ $T-(Z)_n^*$ groups may be independently any of the groups noted above.

More preferred organic acetylenic compounds include

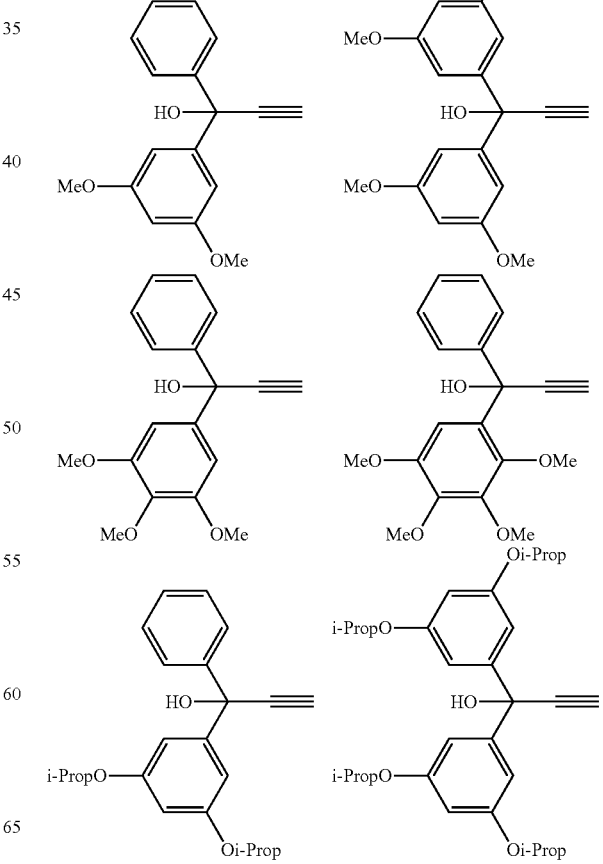

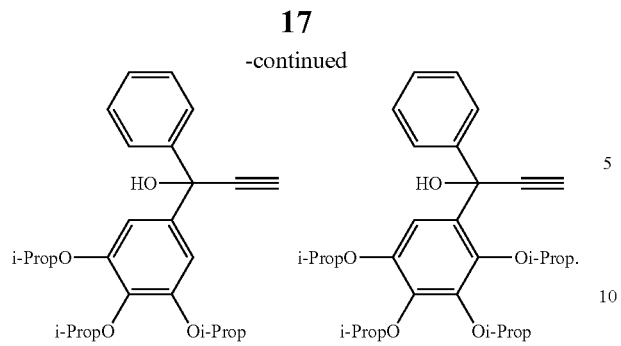

The metathesis catalysts can be formed in-situ with or without the need to isolate and purify prior to use in performing a metathesis reaction with an olefin or olefinic compound. A representative example of the in-situ catalyst formation reaction is as shown below,

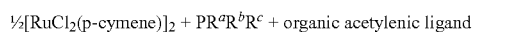

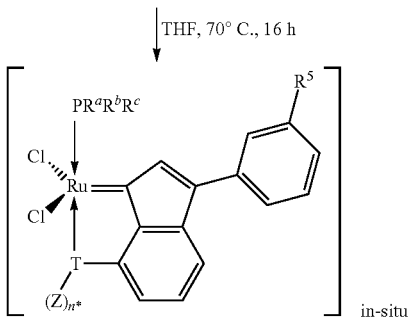

wherein $R^a$, $R^b$, $R^c$, $R^5$, T and Z and $n*$ have been defined above.

In the foregoing molecular structures and formulae, Ph represents phenyl, Cy represents cyclohexyl, Me represents methyl, nBu represents n-butyl, i-Pr represents isopropyl, py represents pyridine (coordinated through the N atom), Mes represents mesityl (i.e., 2,4,6-trimethylphenyl) and DIPP represents 2,6-diisopropylphenyl.

Certain specific catalysts according to the invention include:

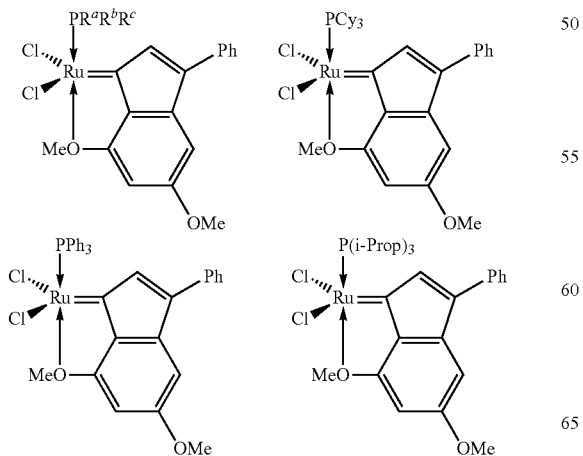

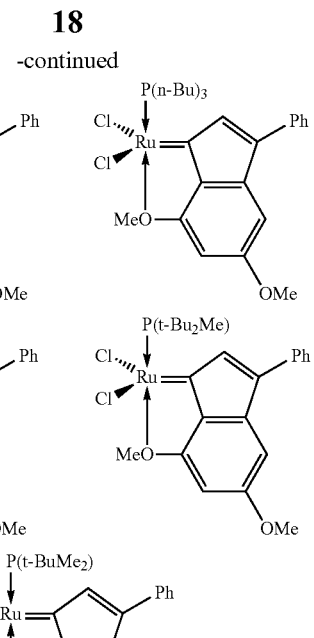

Further specific catalysts according to the invention include, wherein X is any suitable chelating moiety, including, but not limited to O, S, and P, are:

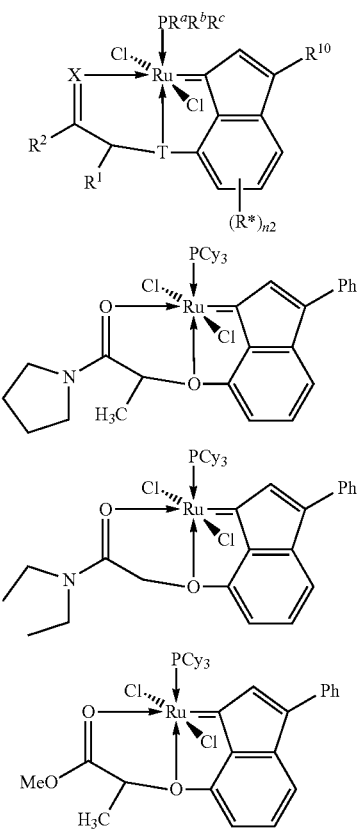

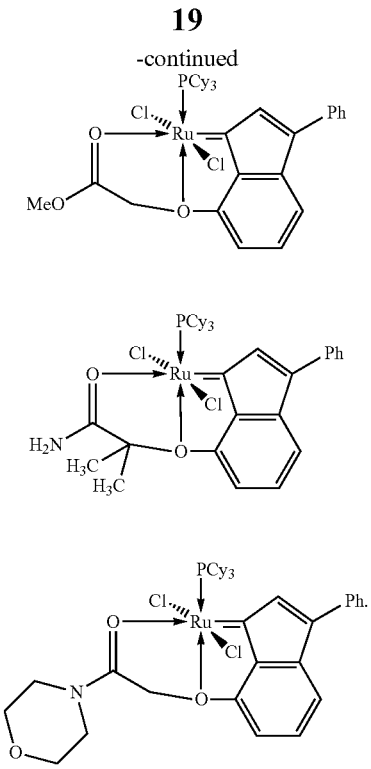

Still other catalysts according to the invention may comprise bis-chelating neutral ligands, as disclosed in WO 2009/124853, incorporated herein by reference.

The methods of the invention may further be used to regenerate decomposed catalyst to provide catalysts according to the invention. For example, decomposed first generation catalysts, such as 1$^{st}$ generation Hoveyda-Grubbs catalysts, may be used to prepare catalysts according to formula (VI) above by reacting the decomposed catalyst with an acetylenic compound (as described above) of the formula

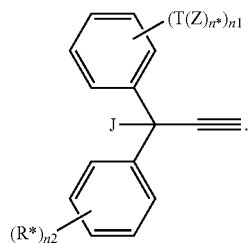

Generally, such reactions may be depicted according to the following Scheme:

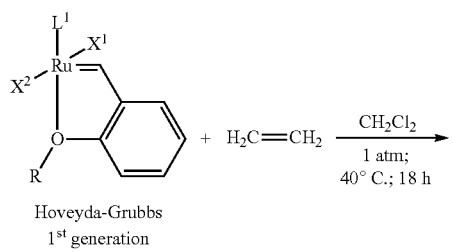

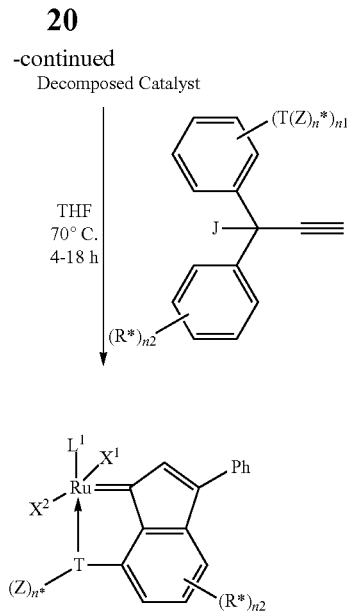

where the variables are described hereinabove.

It is to be understood that while the invention has been described in conjunction with specific embodiments thereof, that the description above as well as the examples included herein are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

Examples

General Information

NMR spectra were recorded on a Bruker 400 MHz NMR spectrometer running Xwin-NMR software. Chemical shifts are reported in parts per million (ppm) downfield from tetramethylsilane (TMS) with reference to internal solvent for $^1$H NMR and $^{13}$C NMR spectra. Chemical shifts are reported in parts per million (ppm) downfield from $H_3PO_4$ for $^{31}$P NMR spectra. All glassware was oven dried and reactions were done under an atmosphere of argon unless otherwise noted. All organic solvents were dried by passage through solvent purification columns containing activated molecular sieves. All other commercial chemicals were used as obtained. Diethyl diallylmalonate was obtained from Sigma-Aldrich. $RuCl_2$(p-cymene)($PCy_3$),[i] N,N-diallyl-4-methyl-benzenesulfonamide,[ii] N-allyl-N-(but-3-enyl)-4-methylbenzenesulfonamide,[iii] and N-allyl-4-methyl-N-(pent-4-enyl) benzene-sulfonamide[iii] were prepared according to literature procedures. N-allyl-N-(hex-5-enyl)-4-methylbenzene-sulfonamide[iii] was prepared from N-allyl-N-hex-5-enyl-amine[iv] following a procedure identical to the synthesis of N,N-diallyl-4-methyl-benzenesulfonamide.

Example 1

Synthesis of 3,5-dimethoxybenzophenone

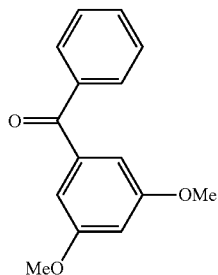 [SMILES: COc1cc(OC)cc(C(=O)c2ccccc2)c1]

This compound was previously prepared by a two-step process.[v] However, we prepared it by a one-step method adapted from another literature procedure.[vi] Neat 3,5-dimethoxybenzonitrile (16.0 g, 98.1 mmol) was added to a 2.0M solution of phenylmagnesium chloride in THF (98.0 mL, 196.1 mmol). The reaction mixture was refluxed for 24 hours at 70° C. The solution was then transferred into a mixture of concentrated aqueous HCl (100 mL) and ice (300 g). The mixture was allowed to warm up to room temperature and stirred for 24 hours. The product was extracted with ether (3×300 mL) and the combined organic layers were washed with brine (200 mL) and water (150 mL) before being dried with anhydrous magnesium sulfate. The filtrate was dried in vacuo to afford 3,5-dimethoxybenzophenone as a yellow solid in 75% yield. $^1$H NMR (CDCl$_3$): δ 7.84 (d, $^3$JH-H=7.2 Hz, 1H), 7.61 (t, $^3$JH-H=7.6 Hz, 2H), 7.50 (t, $^3$JH-H=7.6 Hz, 2H), 6.95 (d, $^3$JH-H=2.4 Hz, 1H), 6.70 (t, $^3$JH-H=2.4 Hz, 2H), 3.85 (s, 6H).

Example 1a

Synthesis of 3,5-diisopropoxybenzophenone

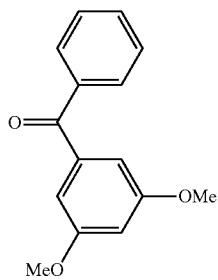 [SMILES: COc1cc(OC)cc(C(=O)c2ccccc2)c1]

3,5-Diisopropoxybenzophenone was prepared from 3,5-diisopropoxybenzonitrile following a procedure analogous to that described above for the preparation of 3,5-dimethoxybenzophenone (Example 1). 3,5-Diisopropoxybenzonitrile was synthesized according to a literature procedure (Wang, E.-C.; Lin, G.-J. A New One Pot Method for the Conversion of Aldehydes into Nitriles Using Hydroxyamine and Phthalic Anhydride. *Tetrahedron Lett.* 1998, 39, 4047-4050).

Example 2

Synthesis of 1-(3,5-Dimethoxyphenyl)-1-Phenylprop-2-yn-1-ol

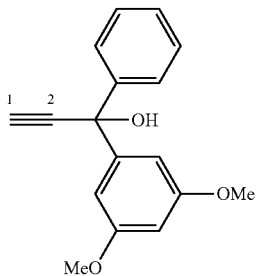 [SMILES: C#CC(O)(c1ccccc1)c1cc(OC)cc(OC)c1]

The following method was adapted from a literature procedure.[vii] Anhydrous THF (50 mL) was cooled to −78° C. Purified acetylene gas was gently bubbled through the THF for 1 hour. A 2.5M solution of n-butyllithium in THF (8.2 mL, 20.5 mmol) was then added drop-wise and the mixture was stirred vigorously for 20 minutes. 3,5-Dimethoxybenzophenone (5.0 g, 20.5 mmol) was dissolved in 10 mL of anhydrous THF and the solution was slowly dropped into the reaction flask. The mixture was stirred vigorously for 20 minutes at −78° C. before being allowed to slowly warm to room temperature. A 5% aqueous solution of NH$_4$Cl (60 mL) was added and the mixture stirred for 30 minutes. The product was extracted with ether (3×100 mL) and the combined organic layers were washed with brine (100 mL) and water (75 mL) before being dried with anhydrous magnesium sulfate. The filtrate was dried in vacuo to afford 1-(3,5-dimethoxyphenyl)-1-phenylprop-2-yn-1-ol as a yellow oil in 95% yield. $^1$H NMR (CDCl$_3$): δ 7.62 (d, $^3$JH-H=7.2 Hz, 2H), 7.33 (t, $^3$JH-H=6.4 Hz, 2H), 7.29 (d, $^3$JH-H=7.2 Hz, 1H), 6.79 (d, $^3$JH-H=2.4 Hz, 2H), 6.37 (t, $^3$JH-H=2.4 Hz, 2H), 3.76 (s, 6H), 3.16 (s, 1H), 2.85 (s, 1H). $^{13}$C{1H} NMR (CDCl$_3$): δ 160.68, 146.99, 144.35, 128.39, 127.99, 126.03, 104.60, 99.84, 86.45 (C2), 75.56 (C1), 74.33, 55.46. HR-MS (FAB+) Calculated for C$_{17}$H$_{17}$O$_3$, 269.1172. found, 269.1178.

Example 2a

Synthesis of 1-(3,5-Diisopropoxyphenyl)-1-Phenylprop-2-yn-1-ol

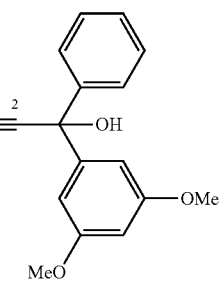

1-(3,5-Diisopropoxyphenyl)-1-Phenylprop-2-yn-1-ol was prepared in an analogous procedure according to Example 2 using 3,5-diisopropoxybenzophenone in place of 3,5-dimethoxybenzophenone.

Example 3

Synthesis of $^{13}C_2$-Labeled 1-(3,5-Dimethoxyphenyl)-1-Phenylprop-2-yn-1-ol

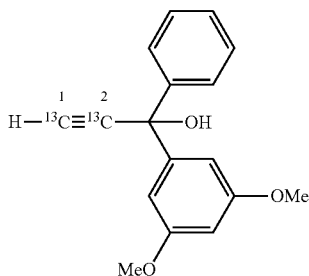 [SMILES: COc1cc(OC)cc(C(O)([13C]#[13CH])c2ccccc2)c1]

A dry 100 mL reaction flask equipped with a stir bar was charged with anhydrous THF (20 mL) inside the glove box, capped with a septum, and taken out of the glove box. The THF was then frozen in a liquid $N_2$ bath and evacuated before doubly labeled acetylene $^{13}C_2H_2$ (0.5 L, 20.4 mmoles) was transferred into the reaction flask via the vacuum line. The flask was filled with Ar and warmed to −78° C. in an acetone/dry ice bath. A 2.5M solution of n-butyl lithium in hexanes (4.1 mL, 10.2 mmoles) was added dropwise under stirring and the reaction mixture was stirred for 20 minutes at −78° C. A suspension of 3,5-dimethoxybenzophenone (2.49 g, 10.2 mmol) in 5 mL of anhydrous THF was added dropwise and the reaction mixture was stirred at −78° C. for 30 minutes. The solution was then allowed to slowly warm up to room temperature and the reaction was worked up in a manner analogous to the procedure for the preparation of 1-(3,5-dimethoxyphenyl)-1-phenylprop-2-yn-1-ol. $^{13}C_2$-1-(3,5-dimethoxyphenyl)-1-phenylprop-2-yn-1-ol was obtained as a faint-yellow crystalline material in 89% yield. $^1H$ NMR (CDCl$_3$): δ 7.62 (d, $^3J_{H-H}$=7.2 Hz, 2H), 7.33 (t, $^3J_{H-H}$=6.4 Hz, 2H), 7.29 (d, $^3J_{H-H}$=7.2 Hz, 1H), 6.79 (d, $^3J_{H-H}$=2.4 Hz, 2H), 6.37 (t, $^3J_{H-H}$=2.4 Hz, 2H), 3.75 (s, 6H), 2.85 (dd, $^1J_{C-H}$=250.4 Hz, $^2J_{C-H}$=50.0 Hz, 1H), protons from OH group not observed. $^{13}C\{^1H\}$ NMR (CDCl$_3$): δ 160.68, 128.39, 127.99, 126.03, 104.60, 99.84, 86.45 (d, $^1J_{C-C}$=171 Hz, C2), 75.56 (d, $^1J_{C-C}$=172 Hz, C1), 55.46.

Example 4

In-Situ Preparations of Olefin Metathesis Catalysts Using 1-(3,5-Dimethoxyphenyl)-1-Phenylprop-2-yn-1-ol Method 1: A small conical vial equipped with a spin vane was charged with RuCl$_2$(p-cymene)(PCy$_3$) (50 mg, 0.085 mmol) and 1-(3,5-dimethoxyphenyl)-1-phenylprop-2-yn-1-ol (5) (25 mg, 0.094 mmol, 1.1 equiv). THF was added to reach a total volume of 1.0 mL of dark orange solution. The vial was sealed, removed from the glove box, and heated at 70° C. under stirring for 16 hours. The dark brown solution was used as is to catalyze ring-closing metathesis (RCM) reactions (see below). The dark brown solution features two main phosphorus-containing species in a ~5/1 ratio according to $^{31}P$ NMR spectroscopy. Major species: $^{31}P\{^1H\}$ NMR (THF-d$_8$): δ 48.6 (s). Minor species: $^{31}P\{^1H\}$ NMR (THF-d$_8$): δ 68.1 (s).

According to Method 1, Schema 3(a), 1-(3,5-dimethoxyphenyl)-1-phenylprop-2-yn-1-ol (5) was reacted with RuCl$_2$(p-cymene)(PCy$_3$) (Method 1; Scheme 3a) or with [RuCl$_2$(p-cymene)]$_2$ in the presence of one equivalent of PCy$_3$ (Method 2; Scheme 3b) to yield ruthenium-indenylidene complex 6 as a major product, according to NMR spectroscopy. The resulting dark-brown solution was subsequently used without any further treatment to promote the ring-closing metathesis (RCM) of diethyl diallylmalonate (eq 2).

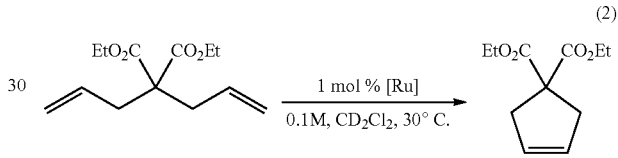

(2)

The in-situ catalyst proved as effective in this RCM as highly active 2a under standard conditions regardless of which method was used to generate it (FIG. 1).

Method 2: A small conical vial equipped with a spin vane was charged with [RuCl$_2$(p-cymene)]$_2$ (52 mg, 0.085 mmol), 1-(3,5-dimethoxyphenyl)-1-phenylprop-2-yn-1-ol (5) (55 mg, 0.206 mmol, 1.2 equiv/Ru), and tricyclohexylphosphine (48 mg, 0.17 mmol, 1.0 equiv/Ru). THF was added to reach a total volume of 2.0 mL of dark orange suspension. The vial was sealed, removed from the glove box, and heated at 70° C. under stirring for 16 hours. The dark brown solution was used as is to catalyze RCM reactions (see below). $^{31}P$ NMR spectroscopy reveals that this solution contains the same species in the same ratio as what was obtained with method 1.

Scheme 3. In-situ formation of catalyst 6

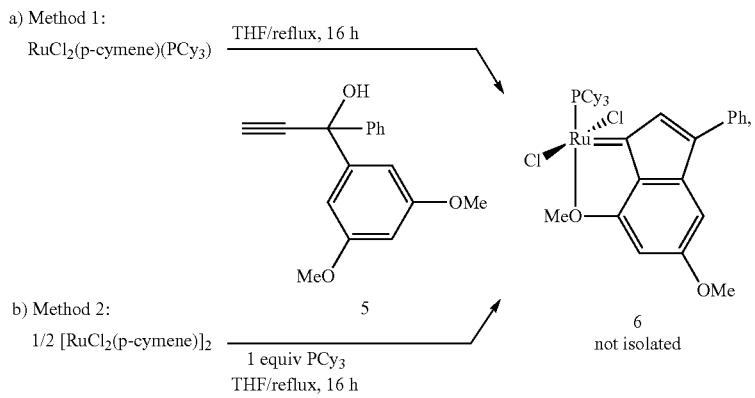

Method 3: A small conical vial equipped with a spin vane was charged with RuCl$_2$(PPh$_3$)$_3$ (165 mg, 0.17 mmol), 1-(3,5-dimethoxyphenyl)-1-phenylprop-2-yn-1-ol (5) (55 mg, 0.206 mmol, 1.2 equiv/Ru). THF was added to reach a total volume of 2.0 mL of dark orange suspension. The vial was sealed, removed from the glove box, and heated at 70° C. under stirring for 3 hours. Tricyclohexyl-phosphine (48 mg, 0.17 mmol, 1.0 equiv/Ru) was then added at room temperature and the mixture was allowed to stir for 1 h. $^{31}$P NMR spectroscopy reveals that this solution contains complex 6 as a major species.

Example 4a

In-Situ Preparations of Olefin Metathesis Catalysts Using 1-(3,5-Diisopropoxyphenyl)-1-Phenylprop-2-yn-1-ol An analogous procedure according to Method 1, Schema 3a), of Example 4 was used in which 1-(3,5-diisopropoxyphenyl)-1-phenylprop-2-yn-1-ol (7) was reacted with RuCl$_2$(p-cymene)(PCy$_3$) (see Method 1; Scheme 3a) to yield ruthenium-indenylidene complex 8.

According to Method 1, Scheme 3(a), a J-Young NMR tube was charged with a solution of RuCl$_2$(p-cymene)(PCy$_3$) (15 mg, 0.026 mmol) and 1-(3,5-diisopropoxyphenyl)-1-phenylprop-2-yn-1-ol (7, 14 mg, 0.043 mmol, 1.65 equiv) in THF-d$^8$ (400 μL). The NMR tube was sealed, removed from the glove box, and heated at 70° C. for 10 hours to give 8 as a major species. The orange brown solution was used as is to catalyze ring-closing metathesis (RCM) reactions (see below). The orange brown solution features two main phosphorus-containing species according to $^{31}$P NMR spectroscopy: Major organometallic species 8 (>90%): $^{31}$P{$^1$H} NMR (THF-d$_8$): δ 68.0 (s). Minor organometallic species (<10%): $^{31}$P{$^1$H} NMR (THF-d$_8$): δ 48.6 (s).

Scheme 3. In-situ formation of catalyst 8

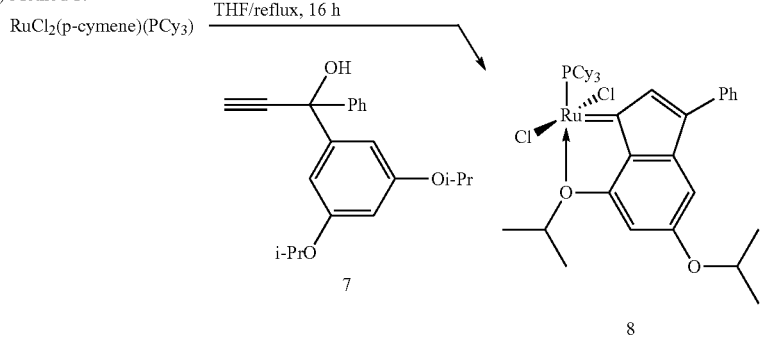

Example 5

In-Situ Preparations of Olefin Metathesis Catalysts Using 13C$_2$-Labelled 1-(3,5-Dimethoxyphenyl)-1-Phenylprop-2-yn-1-ol A solution of $^{13}$C-labeled catalyst was prepared by method 1 (see above) using the $^{13}$C-labelled 1-(3,5-dimethoxyphenyl)-1-phenylprop-2-yn-1-ol ($^{13}$C$_2$-5). This solution contains the same major and minor species as described above according to $^{31}$P NMR spectroscopy. Furthermore, the $^{13}$C and $^{31}$P NMR data are consistent with a mono-phosphine ruthenium indenylidene structure (6) for the major species. Indeed, the shifts in the $^{13}$C NMR spectrum for the C$_\alpha$ and the C$_\beta$ are consistent with an indenylidene fragment as opposed to an allenylidene one.[viii] Additionally, the splitting (doublet of doublet) of the resonance corresponding to the C$_\alpha$ of the major species indicates that only one phosphine ligand is attached to the ruthenium. Major species: $^{13}$C{$^1$H} NMR (THF-d$_8$): δ 287.0 ppm (dd, $^2J_{C\alpha-P}$=11 Hz, $^1J_{C\alpha-C\beta}$=49 Hz, C$_a$), 129.2 ppm (d, $^1J_{C\alpha-C\beta}$=51 Hz, C$_\beta$). $^{31}$P{$^1$H} NMR (THF-d8): δ 48.6 (d, $^2J_{P-C\beta}$=11 Hz). Minor species: $^{13}$C{$^1$H} NMR (THF-d$_8$): δ 256.2 ppm (dd, $^2J_{C\alpha-P}$=15 Hz, $^1J_{C\alpha-C\beta}$=48 Hz, C$_a$), 138.2 ppm (d, $^1J_{C\alpha-C\beta}$=49 Hz, C$_\beta$). $^{31}$P{$^1$H} NMR (THF-d$_8$): δ 68.1 (d, $^2J_{C\alpha-C\beta}$=15 Hz).

Example 6

Procedure for Activity Plots of the RCM of Diethyl Diallylmalonate at 30° C.[ix]

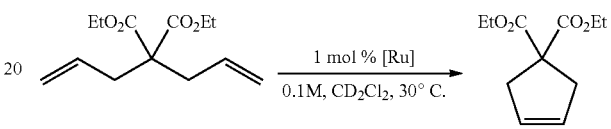

A solution of the olefin metathesis catalyst—prepared by method 1 or method 2 as described above—(0.085M, 6 μL, 0.51 μmol) and CD$_2$Cl$_2$ (480 μL) were transferred to an NMR tube equipped with a screw-cap septum top. The sample was equilibrated at 30° C. in the NMR probe before diethyl diallylmalonate (12 μL, 12 mg, 50 μmol, 0.1M) was added via syringe. Data points were collected over a period of 1 hour. The conversion to the RCM product was determined by comparing the ratio of the integrals of the methylene protons in the substrate material, δ2.61 (dt), with those in the product, δ2.98 (s).

Example 7

Synthesis Procedure for the RCM of Diethyl Diallylmalonate Using Catalyst 6 at 40° C.

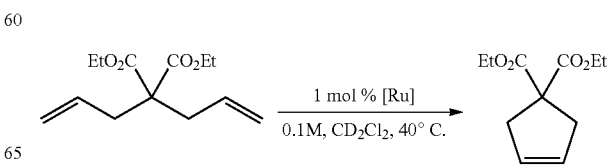

A 0.1M stock solution of diethyl diallylmalonate in CD$_2$Cl$_2$ was prepared by dissolving diethyl diallylmalonate (60 mg, 0.25 mmol) in 2.44 mL of CD$_2$Cl$_2$. A portion of this stock solution (0.5 mL, 50 μmol of diethyl diallylmalonate) was transferred to an NMR tube equipped with a screw-cap septum top. A solution of the olefin metathesis catalyst—prepared by method 1 or method 2 as described above—(0.085M, 6 μL, 0.51 μmol, 1.0 mol %) was added to the diethyl diallylmalonate solution via syringe. The NMR tube was then capped and placed in an oil bath regulated at 40° C. and the reaction mixture was analyzed by $^1$H NMR spectroscopy after a period of time. The extent of conversion of the RCM was determined by comparing the ratio of the integrals of the methylene protons in the substrate, δ2.61 (dt), with those in the product, δ2.98 (s).

Example 7a

Synthesis Procedure for the RCM of Diethyl Diallylmalonate Using Catalyst 8 at 40° C.

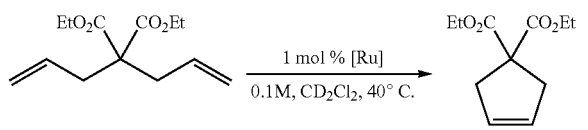 [SMILES: C=CCC(CC=C)(C(=O)OCC)C(=O)OCC ; CCOC(=O)C1(C(=O)OCC)CC=CC1]

A screw-cap NMR tube was charged with diethyl diallylmalonate (20 mg, 0.083 mmol) and CDCl$_3$ (500 μL). A 0.064M solution of catalyst 5 (10 μL, 6.4×10$^{-4}$ mmol, 0.77 mol %) prepared in situ in THF-d$_8$ was added by syringe and the mixture was heated at 40° C. for 30 minutes, after which $^1$H NMR spectroscopy revealed close-to-full conversion (>97%) to the RCM product (by comparing the ratio of the integrals of the methylene protons in the substrate material at δ 2.61 with those in the product at δ 2.99). (see, e.g., Ritter, T.; Hejl, A.; Wenzel, A. G.; Funk, T. W.; Grubbs, R. H. *Organometallics* 2006, 25, 5740-5745 for procedural details)

Example 8

Synthesis Procedure for the RCM of N,N-diallyl-4-methylbenzenesulfonamide

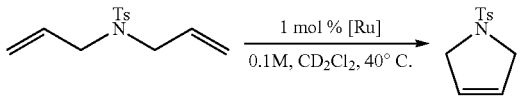

A 0.1M solution of N,N-diallyl-4-methylbenzenesulfonamide in CD$_2$Cl$_2$ was prepared by dissolving N,N-diallyl-4-methylbenzenesulfonamide (12.5 mg, 50 μmol) in 480 μL of CD$_2$Cl$_2$. A solution of the olefin metathesis catalyst—prepared by method 2 as described above—(0.085M, 6 μL, 0.51 μmol, 1.0 mol %) was added to the N,N-diallyl-4-methylbenzenesulfonamide solution via syringe. The solution was transferred to an NMR tube equipped with a screw-cap septum top. The NMR tube was then capped and placed in an oil bath regulated at 40° C. After 1 hour, the reaction mixture was analyzed by $^1$H NMR spectroscopy to reveal full conversion to the RCM product (no substrate and no side-product detected).

Example 9

Synthesis Procedure for the RCM of N-allyl-N-(but-3-enyl)-4-methylbenzenesulfonamide

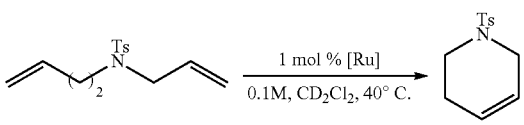

A 0.1M solution of N-allyl-N-(but-3-enyl)-4-methylbenzenesulfonamide in CD$_2$Cl$_2$ was prepared by dissolving N-allyl-N-(but-3-enyl)-4-methylbenzenesulfonamide (13.3 mg, 50 μmol) in 480 μL of CD$_2$Cl$_2$. A solution of the olefin metathesis catalyst—prepared by method 2 as described above—(0.085M, 6 μL, 0.51 μmol, 1.0 mol %) was added to the N-allyl-N-(but-3-enyl)-4-methylbenzenesulfonamide solution via syringe. The solution was transferred to an NMR tube equipped with a screw-cap septum top. The NMR tube was then placed in an oil bath regulated at 40° C. After 1 hour, the reaction mixture was analyzed by $^1$H NMR spectroscopy to reveal full conversion to the RCM product (no substrate and no side-product detected).

Example 10

Synthesis Procedure for the RCM of N-allyl-N-(pent-4-enyl)-4-methylbenzenesulfonamide

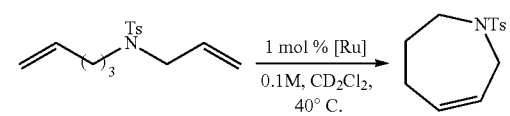

A 0.1M solution of N-allyl-N-(pent-4-enyl)-4-methylbenzenesulfonamide in CD$_2$Cl$_2$ was prepared by dissolving N-allyl-N-(pent-4-enyl)-4-methylbenzenesulfonamide (14.0 mg, 50 μmol) in 480 μL of CD$_2$Cl$_2$. A solution of the olefin metathesis catalyst—prepared by method 2 as described above—(0.085M, 6 μL, 0.51 μmol, 1.0 mol %) was added to the N-allyl-N-(pent-4-enyl)-4-methylbenzenesulfonamide solution via syringe. The solution was transferred to an NMR tube equipped with a screw-cap septum top. The NMR tube was then placed in an oil bath regulated at 40° C. After 1 hour, the reaction mixture was analyzed by $^1$H NMR spectroscopy to reveal full conversion to the RCM product (no substrate and no side-product detected).

Example 11

Synthesis Procedure for the RCM of N-allyl-N-(hex-5-enyl)-4-methylbenzenesulfonamide

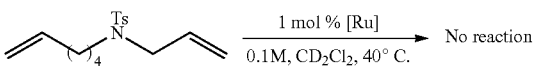

A 0.1M solution of N-allyl-N-(hex-5-enyl)-4-methylbenzenesulfonamide in $CD_2Cl_2$ was prepared by dissolving N-allyl-N-(hex-5-enyl)-4-methylbenzenesulfonamide (14.7 mg, 50 μmol) in 480 μL of $CD_2Cl_2$. A solution of the olefin metathesis catalyst—prepared by method 2 as described above—(0.085M, 6 μL, 0.51 μmol, 1.0 mol %) was added to the N-allyl-N-(hex-5-enyl)-4-methyl-benzenesulfonamide solution via syringe. The solution was transferred to an NMR tube equipped with a screw-cap septum top. The NMR tube was then placed in an oil bath regulated at 40° C. After 2.5 hours, the reaction mixture was analyzed by $^1$H NMR spectroscopy to reveal that no RCM took place (no product detected).

Example 12

Ring-Closing Metathesis (RCM) of Different Substrates

Results of the RCM conversion of different substrates into 5-, 6-, and 7-membered cycloalkanes within 1 hr under mild conditions and low ruthenium loadings are shown in Table 1 (entries 1-5). The cyclization of N-allyl-N-(hex-5-enyl)-4-methylbenzenesulfonamide to yield an eight-membered-ring olefin could not be achieved (Table 1; entry 6), as previously reported for other RCM catalysts (See, Kirkland, T. A.; Grubbs, R. H. *J. Org. Chem.* 1997, 62, 7310-7318).

TABLE 1

RCM with catalyst prepared in-situ by methods 1 and 2

| entry | substrate | product | time (min) | conv. (%) |
|---|---|---|---|---|
| 1[a] | EtO$_2$C, CO$_2$Et diene | EtO$_2$C, CO$_2$Et cyclopentene | 30 | >97[c] |
| 2[b] | EtO$_2$C, CO$_2$Et diene | EtO$_2$C, CO$_2$Et cyclopentene | 60 | >95 |
| 3[b] | Ts-N diallyl | Ts-N pyrroline | 60 | >97[c] |
| 4[b] | Ts-N (CH$_2$)$_2$ | Ts-N tetrahydropyridine | 60 | >97[c] |
| 5[b] | Ts-N (CH$_2$)$_3$ | Ts-N azepine | 60 | >95 |
| 6[b] | Ts-N (CH$_2$)$_4$ | N/A | 150 | 0 |

Conditions: $CD_2Cl_2$, 0.1M substrate, 1 mol % ruthenium, 40° C., Ar;
[a]catalyst prepared in-situ according to method 1;
[b]catalyst prepared in-situ according to method 2;
[c]no substrate was detected by $^1$H NMR spectroscopy.

Example 13

In-Situ Catalyst Stability

To investigate the stability of the in-situ catalysts prepared according to the invention, a solution of catalyst prepared by method 2 was stored in a vial under argon at room temperature for 2 weeks and then used in the RCM of diethyl diallylmalonate within 30 min at 40° C. as a freshly prepared solution (Table 2). The stored catalyst was shown to give essentially the same RCM conversion as un-stored catalyst.

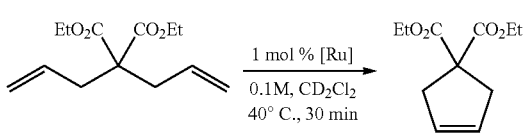

TABLE 2

Stability study of the in-situ catalyst solution.

| | Duration of storage of the catalyst solution[a] | | | |
|---|---|---|---|---|
| | 0 day | 5 days | 9 days | 14 days |
| Conversion | 94% | 94% | 94% | 95% |

[a]the catalyst solution was prepared by method 2 and stored in a vial under argon at 22° C.

Although not limited thereto, the results included herein demonstrate the use of a derivative of 1,1-diphenylprop-2-yn-1-ol that contains electron-donating substituents in the meta positions of one phenyl group (5) to generate a new olefin metathesis catalyst in situ via a simple one-step procedure. As is disclosed herein more generally, the invention provides new catalysts that are as active as a commercial first-generation Hoveyda-Grubbs catalyst (2a) at promoting the formation of disubstituted five-, six-, and seven-membered ring cycloalkenes and are stable in solution for at least two weeks.

Example 14a

Generation of Olefin Metathesis Catalyst 6 from Decomposed Catalyst

A 50 mL round bottom reaction flask equipped with a stir bar was charged with the Hoveyda-Grubbs 1$^{st}$ generation catalyst (0.5 g, 0.83 mmol) and dichloromethane (10 mL). The solution was exposed to ethylene (1 atm) and heated at 40° C. under stirring for 18 hours to decompose the Hoveyda-Grubbs 1$^{st}$ generation catalyst. The decomposed catalyst (i.e., the ruthenium-containing decomposition product) was isolated by evaporating the dichloromethane, triturating with pentane, filtering and drying the solid under vacuum. The decomposed catalyst (25 mg) was treated with 1-(3,5-dimethoxyphenyl)-1-phenylprop-2-yn-1-ol (5, 30 mg, 0.11 mmol) in THF-d$^8$ (400 μL) at 70° C. for 4 hours according to Scheme 4 to give 6 as the major ruthenium-containing species (according to NMR spectroscopy).

Scheme 4:

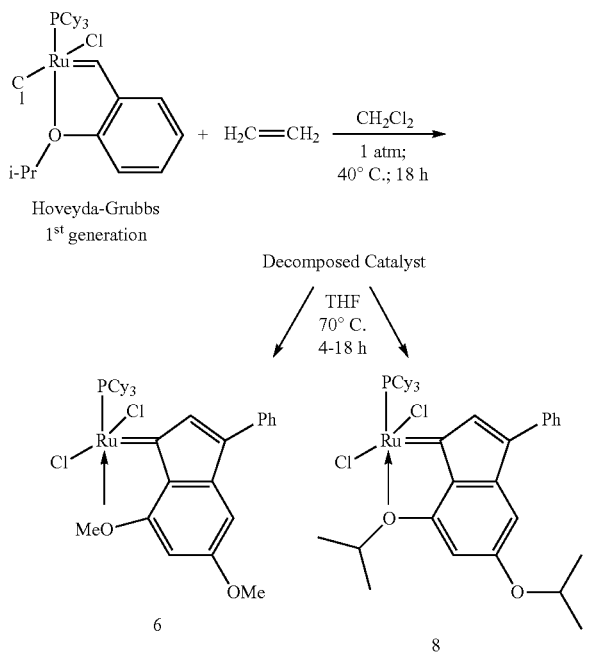

Hoveyda-Grubbs 1st generation

Example 14b

Generation of Olefin Metathesis Catalyst 8 from Decomposed Catalyst

A 50 mL round bottom reaction flask equipped with a stir bar was charged with the Hoveyda-Grubbs 1st generation catalyst (0.5 g, 0.83 mmol) and dichloromethane (10 mL). The solution was exposed to ethylene (1 atm) and heated at 40° C. under stirring for 18 hours to decompose the Hoveyda-Grubbs 1$^{st}$ generation catalyst. The decomposed catalyst (i.e., the ruthenium-containing decomposition product) was isolated by evaporating the dichloromethane, triturating with pentane, filtering and drying the solid under vacuum. The decomposed catalyst (25 mg) was treated with 1-(3,5-diisopropoxyphenyl)-1-phenylprop-2-yn-1-ol (7, 36 mg, 0.11 mmol) in THF-d$^8$ (400 μL) at 70° C. for 4 hours according to Scheme 4 shown in Example 14a to give 8 as the major ruthenium-containing species (according to NMR spectroscopy).

References Cited in the Examples i Demonceau, A.; Stumpf, A. W.; Saive, E.; Noels, A. F. *Macromolecules* 1997, 30, 3127-3136.
ii Paquette, L. A. *J. Org. Chem.* 2006, 71, 8438-8445.
iii Lipshutz, H. B.; Ghorai, S. *Org. Lett.* 2009, 11, 3, 705-708.
iv Marks, T. J. *J. Am. Chem. Soc.* 1998, 120, 1757-1771.
v Krishnamurthy, M.; Ferreira, A. M.; Moore, B. M., II *Bioorg. Med. Chem. Lett.* 2003, 13, 3487-3490.
vi Bachmann, W. E.; Ferguson, J. W. *J. Am. Chem. Soc.* 1934, 56, 2081-2084.
vii Michel Treilhou. *J. Org. Chem.* 1992, 57, 3203-3208.
viii For NMR data on ruthenium indenylidene complexes, see: Fürstner, A.; Guth, O.; Duffels, A.; Seidel, G.; Liebl, M.; Gabor, B.; Mynott, R., *Chem.-Eur. J.* 2001, 7, 4811-4820. For NMR data on ruthenium allenylidene complexes, see: Schanz, H.-J.; Jafarpour, L.; Stevens, E. D.; Nolan, S. P., *Organometallics* 1999, 18, 5187-5190.
ix Ritter, T.; Hejl, A.; Wenzel, A. G.; Funk, T. W.; Grubbs, R. H. *Organometallics* 2006, 25, 5740-5745.

What is claimed is:

1. A method for synthesizing an organometallic compound of the formula

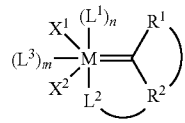

comprising contacting a precursor compound of the formula $(X^1X^2ML_jL^1_kL^3_m)_i$ with an acetylenic compound comprising a chelating moiety, optionally, in the presence of a neutral electron donor $L^1$; wherein M is a Group 8 transition metal;

L, $L^1$, $L^2$, and $L^3$ are neutral electron donors;

j is 1, 2, or 3; k is zero, 1, or 2; m is zero or 1; n is 1 or 2; and i is an integer; with the proviso that k is zero when the precursor compound is contacted with the acetylenic compound in the presence of the neutral electron donor $L^1$;

$X^1$ and $X^2$ are anionic ligands; and $R^1$ and $R^2$ are independently selected from hydrocarbyl, substituted hydrocarbyl, heteroatom-containing hydrocarbyl, substituted heteroatom-containing hydrocarbyl, and functional groups, wherein $R^1$ and $R^2$ are linked and together form one or more cyclic groups, $R^2$ and $L^2$ are linked and together form one or more cyclic groups, and any other two or more of $X^1$, $X^2$, $L^1$, $L^2$, $L^3$, $R^1$, and $R^2$ can be taken together to form one or more cyclic groups.

2. The method of claim 1, wherein M is Ru or Os.

3. The method of claim 1, wherein $L^1$, $L^2$, and $L^3$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, thioether, and thiocarbonyl.

4. The method of claim 3, wherein the phosphine is of the formula $PR^aR^bR^c$, wherein $R^a$, $R^b$, and $R^c$ are each independently selected from aryl, substituted aryl, alkyl, substituted alkyl, cycloalkyl, substituted cycloalkyl, heterocycles, and substituted heterocycles.

5. The method of claim 1, wherein $X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and $C_5$-$C_{20}$ aryl.

6. The method of claim 1, wherein the acetylenic compound comprising a chelating moiety is a compound having the structure

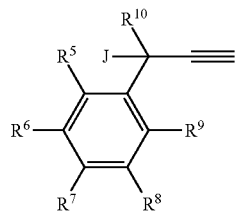

wherein,
- J is a leaving group selected from hydroxyl, halide, ester, perhalogenated phenyl, acetate, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, and $C_1$-$C_6$ alkylsulfonyl;
- $R^5$, $R^6$, $R^7$, $R^8$, and $R^9$ are each independently selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, and any combination of $R^5$, $R^6$, $R^7$, $R^8$, and $R^9$ can be linked to form one or more cyclic groups; and wherein $R^5$, $R^6$, $R^7$, $R^8$, and $R^9$ may contain -T-(Z)n*, wherein,
- T is a heteroatom selected from N, O, S, and P;
- Z is selected from hydrogen, alkyl, aryl, functionalized alkyl, and functionalized aryl, wherein the functional group(s) are independently selected from alkyl, aryl, alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; and n* is 1 or 2, such that n* is 1 for the divalent heteroatoms O or S, and n* is 2 for the trivalent heteroatoms N or P; and
- $R^{10}$ is selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, and wherein when $R^{10}$ is aryl or heteroaryl, $R^{10}$ may be substituted with any combination of $R^5$, $R^6$, $R^7$, $R^8$ and $R^9$ and can be linked with any of $R^5$, $R^6$, $R^7$, $R^8$, and $R^9$ to form one or more cyclic groups.

7. The method of claim 6, wherein the acerylenic compound comprising a chelating moiety is a compound of the formula

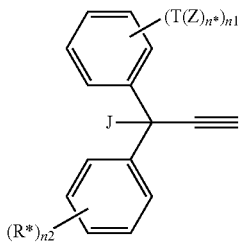

wherein,
- T, Z, and n* are as defined in claim 6;
- n1 is an integer from 1 to 5;
- n2 is an integer from 0 to 5; and
- R* is selected from $R^5$, $R^6$, $R^7$, $R^8$, and $R^9$, or combinations thereof, as defined in claim 6.

8. The method of claim 1, wherein the organometallic compound is of the formula

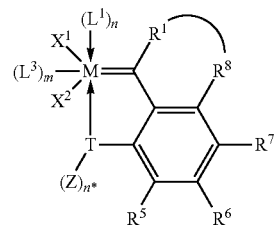

wherein, M, $L^1$, $L^3$, $X^1$, $X^2$, $R^1$, n, and m are as defined in claim 1;
- $R^5$, $R^6$, $R^7$, and $R^8$ are each independently selected from hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, wherein $R^1$ and $R^8$ are linked and together form one or more cyclic groups, and any combination of $R^1$, $R^5$, $R^6$, $R^7$, and $R^8$ can be linked to form one or more cyclic groups;
- T is a heteroatom selected from N, O, S, and P;
- Z is selected from hydrogen, alkyl, aryl, functionalized alkyl, and functionalized aryl, wherein the functional group(s) are independently selected from alkyl, aryl, alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; and
- n* is 1 or 2, such that n* is 1 for the divalent heteroatoms O or S, and n* is 2 for the trivalent heteroatoms N or P.

* * * * *